US012343135B2

(12) United States Patent
Masuda

(10) Patent No.: US 12,343,135 B2
(45) Date of Patent: Jul. 1, 2025

(54) BED-LEAVING PREDICTION NOTIFICATION DEVICE AND NON-TRANSITORY STORAGE MEDIUM

(71) Applicant: INFIC Inc., Shizuoka (JP)

(72) Inventor: Masatoshi Masuda, Shizuoka (JP)

(73) Assignee: INFIC Inc., Shizuoka (JP)

( * ) Notice: Subject to any disclaimer, the term of this patent is extended or adjusted under 35 U.S.C. 154(b) by 539 days.

(21) Appl. No.: 17/955,875

(22) Filed: Sep. 29, 2022

(65) Prior Publication Data

US 2023/0025313 A1 Jan. 26, 2023

Related U.S. Application Data

(63) Continuation of application No. PCT/JP2021/010144, filed on Mar. 12, 2021.

(30) Foreign Application Priority Data

Mar. 31, 2020 (JP) ................... 2020-064264

(51) Int. Cl.
*A61B 5/11* (2006.01)
*A61B 5/00* (2006.01)
(Continued)

(52) U.S. Cl.
CPC ............ *A61B 5/1115* (2013.01); *A61B 5/002* (2013.01); *A61B 5/0205* (2013.01);
(Continued)

(58) Field of Classification Search
CPC ..... A61B 5/1115; A61B 5/002; A61B 5/0205; A61B 5/6889; A61B 5/7275; A61B 5/024;
(Continued)

(56) References Cited

U.S. PATENT DOCUMENTS 7,786,874 B2 * 8/2010 Rodgers ................ G16H 40/67
705/2
9,165,449 B2 10/2015 Ribble et al.
(Continued)

FOREIGN PATENT DOCUMENTS

CN 102150186 A 8/2011
CN 109394223 A 3/2019
(Continued)

OTHER PUBLICATIONS

Office Action issued in Chinese Patent Application No. 202180025044.8 mailed on Mar. 27, 2024 (27 pages).
(Continued)

*Primary Examiner* — Jonathan T Kuo
(74) *Attorney, Agent, or Firm* — Nakanishi IP Associates, LLC

(57) ABSTRACT

A bed-leaving prediction device (server device) (10) is connected through a digital communication network (60) to: a portable information processing terminal (40) of care staff; environmental sensors (32 to 34) for detecting environment values such as temperature in a room; a human sensor (31); and a bed sensor (35). A bed-leaving prediction processing section (115) calculates a bed-leaving prediction value indicative of a degree of possibility that a care recipient leaves a sleeping furniture after a second time interval has expired since a current time point based on a plurality of environment values detected in a time period between the current time point and a time point before expiration of a first time interval, outputs of the human sensor, and outputs of the bed sensor. A bed-leaving notification processing section (117) compares the bed-leaving prediction value with a threshold value, and transmits, to the portable information processing terminal, a bed-leaving notification indicating that the care recipient leaves the sleeping furniture
(Continued)

after the second time interval expires when the bed-leaving prediction value exceeds the threshold value.

8 Claims, 8 Drawing Sheets

(51) Int. Cl.
*A61B 5/0205* (2006.01)
*G16H 40/20* (2018.01)
*G16H 40/63* (2018.01)

(52) U.S. Cl.
CPC .......... *A61B 5/6889* (2013.01); *A61B 5/7275* (2013.01); *G16H 40/20* (2018.01); *G16H 40/63* (2018.01)

(58) Field of Classification Search
CPC .......... A61B 5/7465; A61B 2560/0242; A61B 5/0004; A61B 5/4809; A61B 5/6892; A61B 5/7267; G16H 40/20; G16H 40/63; G16H 40/67; G16H 50/20; G16H 50/70; A61G 7/05; A61G 12/00; G08B 25/04
See application file for complete search history.

(56) References Cited

U.S. PATENT DOCUMENTS

| | | | |
|---|---|---|---|
| 11,272,860 B2* | 3/2022 | Larson | G16H 70/20 |
| 2007/0136102 A1* | 6/2007 | Rodgers | G06Q 10/087 |
| | | | 348/E7.078 |
| 2011/0156915 A1 | 6/2011 | Brauers et al. | |
| 2014/0253710 A1 | 9/2014 | Yasukawa et al. | |
| 2016/0005289 A1 | 1/2016 | Ribble et al. | |
| 2017/0098360 A1 | 4/2017 | Ribble et al. | |
| 2017/0345275 A1 | 11/2017 | Ribble et al. | |
| 2018/0214051 A1* | 8/2018 | Larson | H04W 4/38 |

FOREIGN PATENT DOCUMENTS

| | | |
|---|---|---|
| JP | 2013-240601 A | 12/2013 |
| JP | 2014-004227 A | 1/2014 |
| JP | 2014-174627 A | 9/2014 |
| JP | 2015-133608 A | 7/2015 |
| JP | 2016-007446 A | 1/2016 |
| JP | 2017-153863 A | 9/2017 |
| JP | 2017-168098 A | 9/2017 |
| WO | 2017-213136 A1 | 12/2017 |

OTHER PUBLICATIONS

International Search Report issued in PCT/JP2021/010144 mailed on Jun. 8, 2021 with English Translation (8 pages).
Written Opinion of International Searching Authority issued in PCT/JP2021/010144 mailed on Jun. 8, 2021 with English Translation (6 pages).
Office Action issued in Japanese Patent Application No. 2022-511775 mailed on Jun. 20, 2023 (8 pages).

* cited by examiner

BED-LEAVING PREDICTION NOTIFICATION DEVICE AND NON-TRANSITORY STORAGE MEDIUM

FIELD

Embodiments described herein relate generally to a bed-leaving prediction notification device and a non-transitory storage medium.

BACKGROUND

In nursing facilities, there have been many incidents where care recipients such as elderly persons fall down and suffer broken bones when they wake up and leave the bed. Further, such risk of falling places a heavy psychological burden on care staff during understaffed night shift.

Currently, a number of facilities have introduced a system that is provided with sensors such as a pressure sensitive mat on each bed and that detects a care recipient leaving the bed and notifies it to a portable terminal of care staff.

However, conventional systems detect that a care recipient left the bed only after the fact, and the care staff could not attend to nor care for the care recipient leaving the bed.

There is a need for notifying care staff of a care recipient leaving the bed, for example, 30 minutes before the care recipient leaves the bed.

SUMMARY OF THE INVENTION

A bed-leaving prediction server device according to an embodiment is connected through a digital communication network to: an information processing terminal for care staff who care for a care recipient; an environmental sensor configured to detect at least one environment value of temperature, humidity, and illuminance in a room where the care recipient stays; an infrared sensor installed to include a sleeping furniture in the room in a sensing area; and a sleeping furniture sensor configured to detect movement of the care recipient on the sleeping furniture. Based on an output of the infrared sensor, the computing section repeatedly computes a movement-amount indicator that depends on the amount of movement of the care recipient on the sleeping furniture. Based on an output of the sleeping furniture sensor, the computing section repeatedly computes a pulse rate of the care recipient, a posture indicator for discerning a posture: lying flat; sitting; or sitting up with legs outstretched, a rolling-over indicator for discerning rolling over: rolling over to left; leftward movement; rightward movement; rolling over to right; or no movement, a body movement indicator for discerning between body movement and resting states, and a sleep indicator for discerning between sleeping and waking. The calculating section calculates a bed-leaving prediction value indicative of a degree of possibility that the care recipient leaves the sleeping furniture after a second time interval has expired since a prediction calculation processing time point based on: a plurality of the environment values detected in a time period between the prediction calculation processing time point and a time point before expiration of a first time interval; and a plurality of the movement-amount indicators, a plurality of the pulse rates, a plurality of the posture indicators, a plurality of the rolling-over indicators, a plurality of the body movement indicators, and a plurality of the sleep indicators, which are computed based on outputs of the sleeping furniture sensor in the time period. The notification processing section compares the bed-leaving prediction value with a threshold value, and transmits a bed-leaving notification to the information processing terminal when the bed-leaving prediction value exceeds the threshold value, the bed-leaving notification indicating that the care recipient leaves the sleeping furniture after the second time interval expires.

DETAILED DESCRIPTION

A bed-leaving prediction notification device according to the embodiment will now be described with reference to drawings. Here, "bed-leaving prediction" is defined as predicting a possibility that a care recipient leaves the bed after relatively long time on the order of 30 minutes, and is clearly distinguished from detecting that a care recipient left the bed after the fact, or even detecting a clear premonition or sign of bed-leaving such as the fact that a care recipient keeps the upper part of the body elevated on the bed or is sitting on an edge of the bed. Once a premonition or sign of bed-leaving is detected, it has been known that the care recipient will leave the bed several seconds later, or at least several minutes later.

Figure 1:
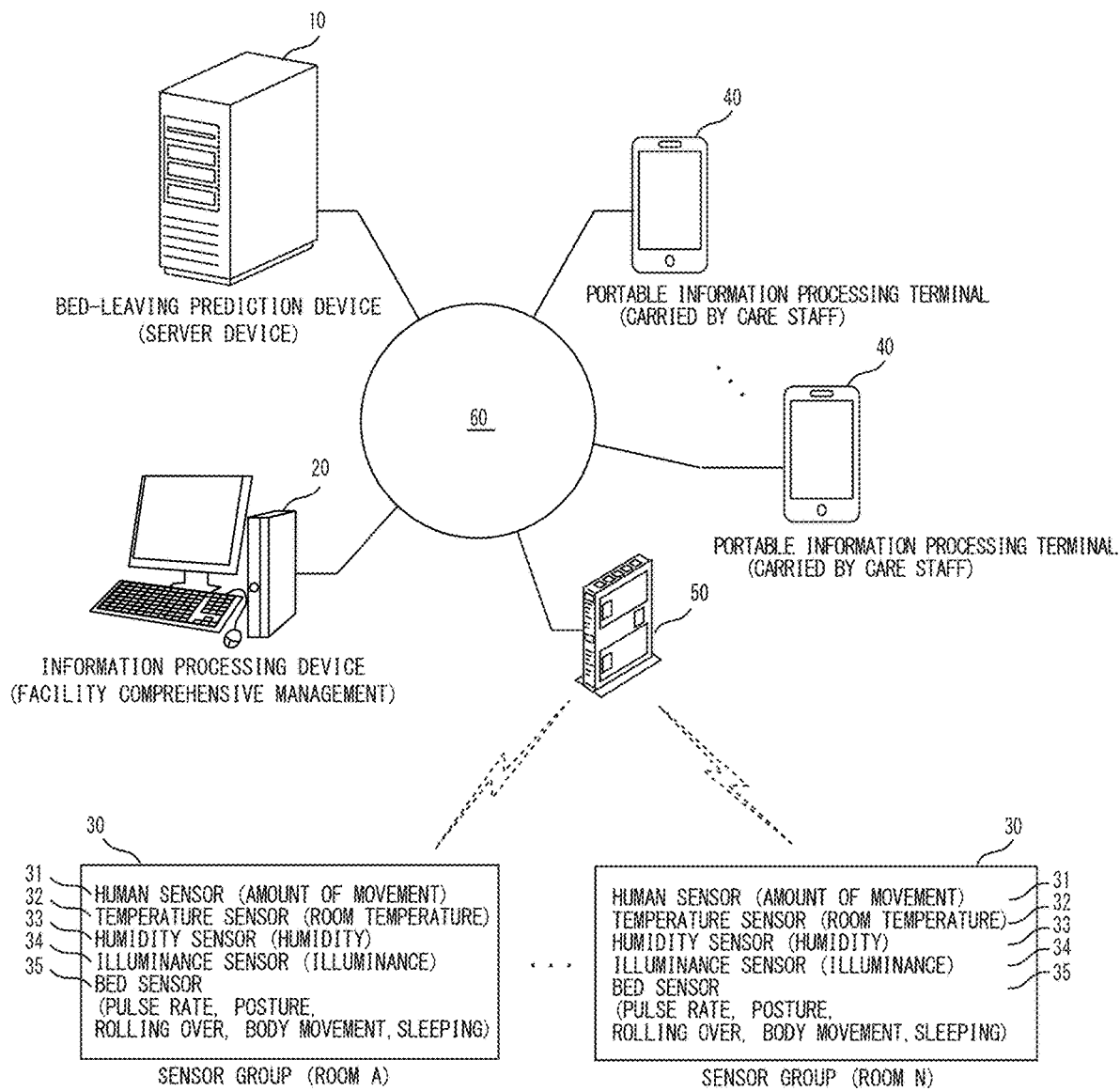
FIG. 1 illustrates the entire system including a bed-leaving prediction notification device according to the embodiment.

As illustrated in FIG. 1, a bed-leaving prediction notification device (information processing device) 10 represented as a server device is connected to a digital communication network 60. The digital communication network 60 is typically a public communication network (Internet network), but this is not a limitation. Through the digital communication network 60, an information processing device 20 for comprehensive management of a nursing facility, and a plurality of portable information processing terminals 40 such as smartphones carried by a plurality of care staff members respectively are connected to the bed-leaving prediction notification device 10. An application for cooperating with the bed-leaving prediction notification device 10 is installed on the portable information processing terminals 40. A sensor group 30 is connected to the bed-leaving prediction notification device 10 through the digital communication network 60 and a gateway device 50. The sensor group 30 and the gateway device 50 are connected together in a wired manner or by a near-field wireless communication system such as Bluetooth (registered trademark), for example.

Figure 2:
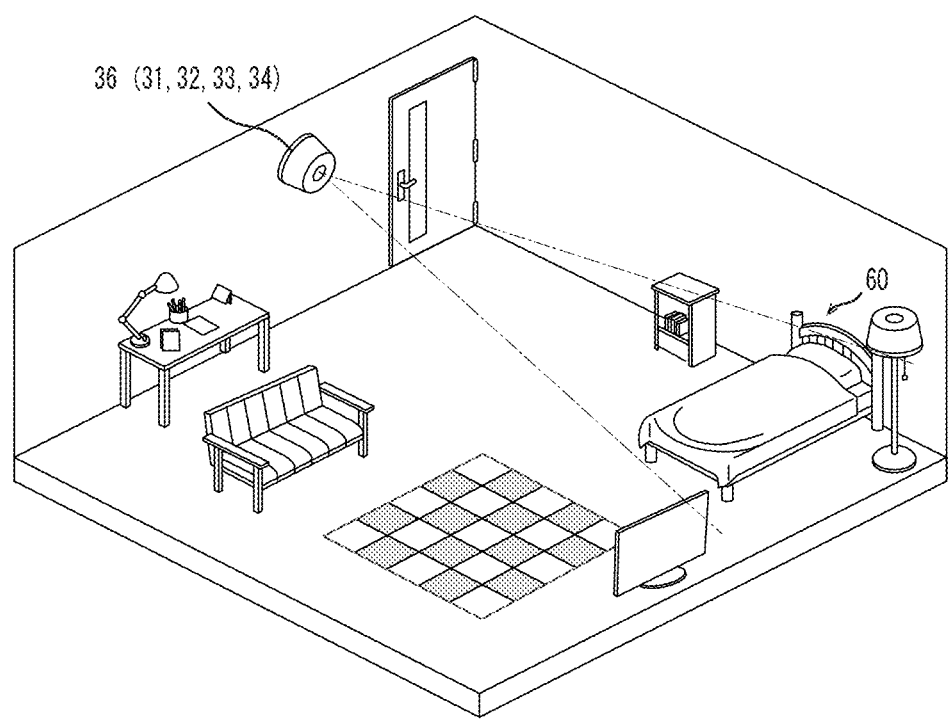
FIG. 2 is a schematic view in a room where the human sensor in FIG. 1 is installed.

In the sensor group 30, there are provided a human sensor 31, a temperature sensor 32, a humidity sensor 33, an illuminance sensor 34, and a bed sensor (sleeping furniture sensor) 35. As illustrated in FIG. 2, the human sensor 31, the temperature sensor 32, the humidity sensor 33, and the illuminance sensor 34 are integrated into, for example, a room sensor 36. The human sensor 31 is typically an infrared sensor. The room sensor 36 is installed on a wall surface or the like in a bird's-eye view manner such that a sensing area (broken line) of the human sensor 31 includes a sleeping furniture (here, a bed) 70 in the room. An output of the human sensor 31 allows to compute a movement-amount indicator that reflects the amount of movement of a care recipient on the sleeping furniture 70.

Figure 3:
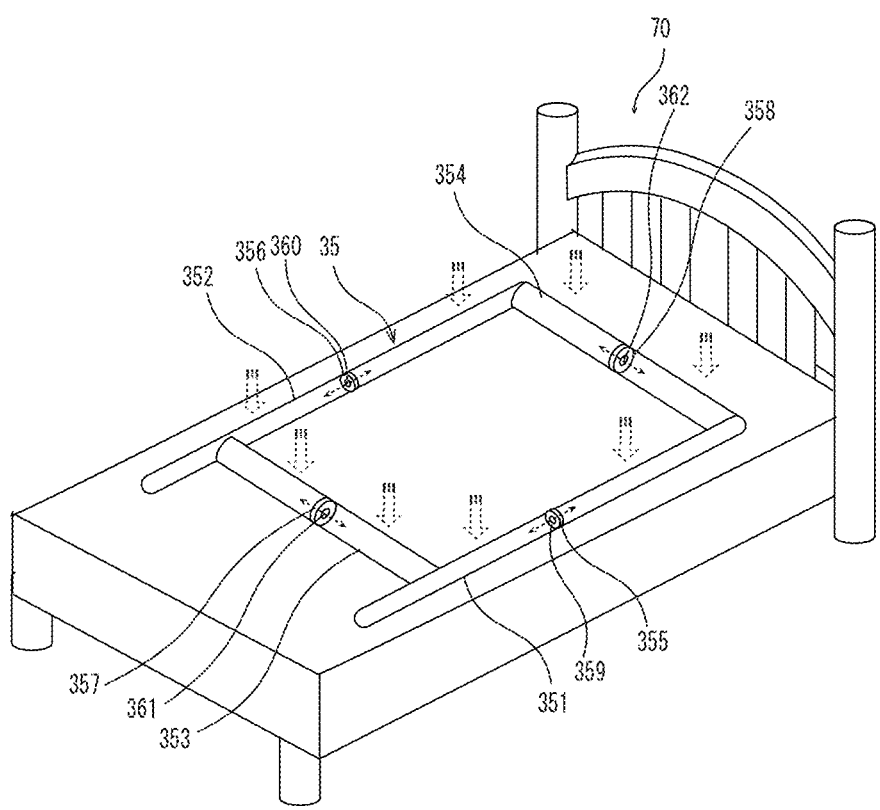
FIG. 3 is a schematic view illustrating the bed sensor in FIG. 1.

The bed sensor 35 is a sleeping furniture sensor for detecting movement due to heartbeats, rolling over or the like of the care recipient on the sleeping furniture 70. As illustrated in FIG. 3, for example, four flexible air tubes 351 to 354 are connected together longitudinally and transversely such that internal spaces are brought into communication with one another to form a single circulative path. The air tubes 351 to 354 are partitioned by diaphragms 355 to 358 at multiple places. Each of the diaphragms 355 to 358 is opened slightly in the center, and microphones 359 to 362 are attached to edges of the openings. In response to movement such as beats or rolling over of the care recipient, air flows within the circulative path of the air tubes 351 to 354. In response to the flow, the microphones 359 to 362 detect acoustic signals generated at the openings of the diaphragms 355 to 358.

Figure 4:
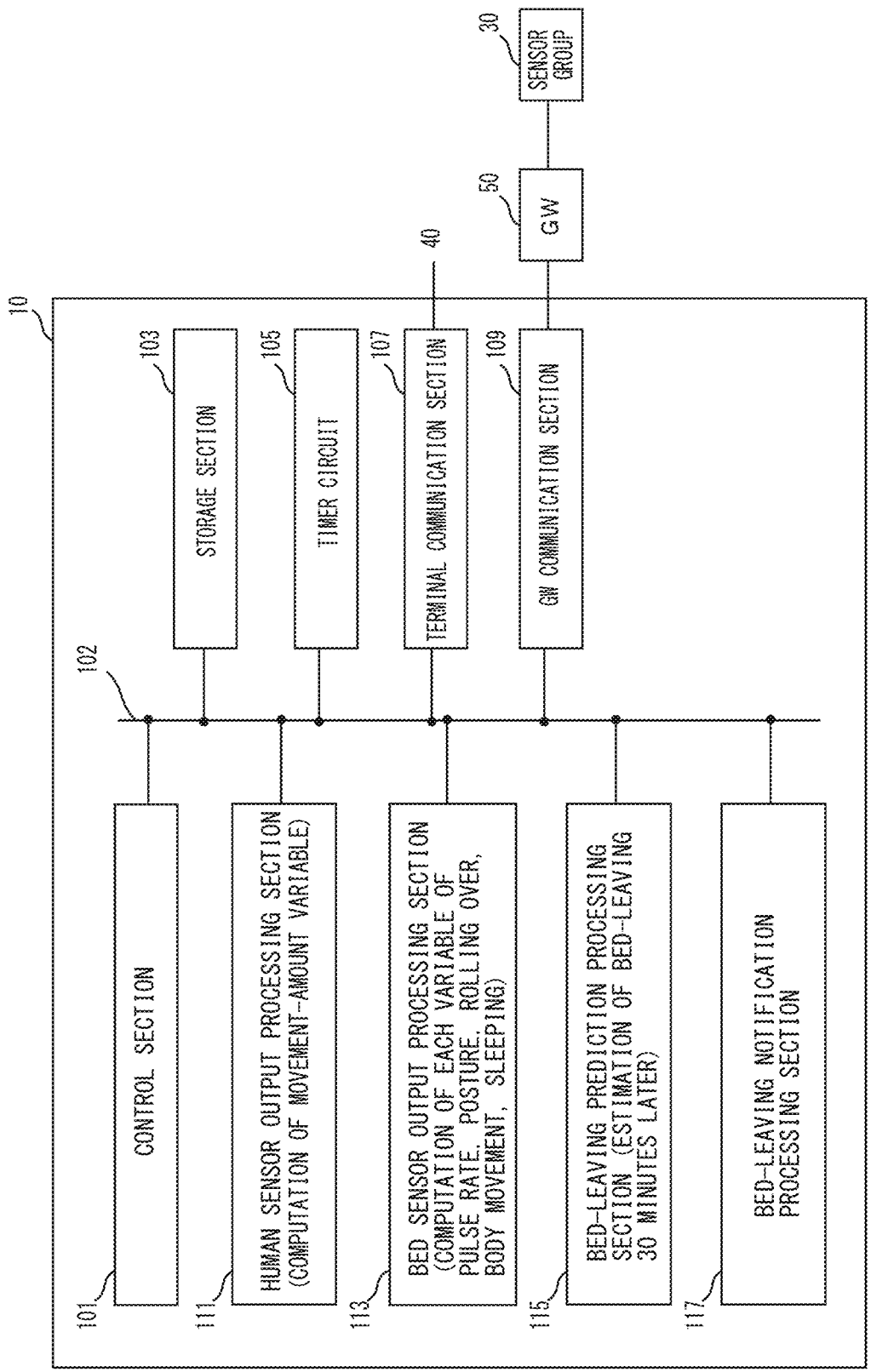
FIG. 4 is a functional block diagram of the bed-leaving prediction notification device in FIG. 1.

As illustrated in FIG. 4, the bed-leaving prediction notification device 10 includes a control section 101 in charge of a general control. Through a control/data bus 102, a storage section 103, a timer circuit 105, a terminal communication section 107, a gateway communication section 109, a human sensor output processing section 111, a bed sensor output processing section 113, a bed-leaving prediction processing section 115, and a bed-leaving notification processing section 117 are connected to the control section 101.

Practical device components for the control section 101, the human sensor output processing section 111, the bed sensor output processing section 113, the bed-leaving prediction processing section 115, and the bed-leaving notification processing section 117 include a central processing unit (CPU), a graphics processing unit (GPU), a random access memory (RAM), and a read only memory (ROM). A bed-leaving overseeing program, a human sensor output processing program, a bed sensor output processing program, a bed-leaving prediction program, and a bed-leaving notification program are stored in the storage section 103, which is composed of a hard disk drive (HDD) or a solid state drive (SSD), in advance. Upon startup, each program is loaded from the storage section 103 into the RAM, so that overseeing processing, human sensor output processing, bed sensor output processing, bed-leaving prediction processing, and bed-leaving notification processing are executed.

The storage section 103 stores data or the like for the sensor group 30, and an association table in which identification numbers (ID) of a plurality of portable information processing terminals 40 carried by a plurality of care staff members who take care of a plurality of care recipients or rooms are associated with the care recipients or rooms respectively. The identification number (ID) is associated with an ID of an application installed on the portable information processing terminal 40. The application ID is used to communicate information between the bed-leaving prediction notification device 10 and the portable information processing terminal 40 bidirectionally.

The human sensor output processing section 111 computes, repeatedly in a predetermined cycle, a movement-amount indicator that reflects the amount of movement of the care recipient on the sleeping furniture 70 based on waveform features such as an integral value per unit time of wave height values and an area of a signal waveform portion per unit time of detected signals of the human sensor 31.

When the care recipient exhibits movement, such as rolling over or beats, on the sleeping furniture 70, air moves in the circulative path in the air tubes 351 to 354 in response to variation in the center of gravity or the distribution of body pressure. The movement is detected by the microphones 359 to 362. According to parameters such as wave height values of output signals of the microphones 359 to 362, temporal variation in the wave height values, and temporal shifts among the wave height values, the bed sensor output processing section 113 computes a pulse rate of the care recipient (heart rate), a value for discerning a posture: lying flat; sitting; or sitting up with legs outstretched (posture indicator), a value for discerning rolling over: rolling over to left; leftward movement; rightward movement; rolling over to right; or no movement (rolling-over indicator), a value for discerning between body movement and resting states (body movement indicator), and a value for discerning between sleeping and waking (sleep indicator).

The bed-leaving prediction processing section 115 calculates, in percent (%), a bed-leaving prediction value indicative of a degree of possibility that the care recipient leaves sleeping furniture 70 after a second time interval has expired, or at least 10 minutes, typically 30 minutes has expired, since the current time point (prediction calculation processing time point), based on:

a plurality of values of temperature repeatedly detected by the temperature sensor 32 in a time period (30 minutes) between the current time point and a time point before expiration of a first time interval, or in at least 10 minutes, typically in a time period between the current time point and a time point before expiration of 30 minutes;

a plurality of values of humidity repeatedly detected by the humidity sensor 33 during the time period;

a plurality of values of illuminance repeatedly detected by the illuminance sensor 34 during the time period;

a plurality of movement-amount indicators indicative of the amount of movement for the care recipient computed by the human sensor output processing section 111 based on a plurality of detected signals repeatedly detected by the human sensor 31 during the time period;

a pulse rate of the care recipient (heart rate) computed by the bed sensor output processing section 113 based on a plurality of detected signals repeatedly detected by the bed sensor 35 during the time period;

a plurality of posture indicators for discerning a posture for the care recipient computed by the bed sensor output processing section 113 based on a plurality of detected signals repeatedly detected by the bed sensor 35 during the time period;

a plurality of rolling-over indicators for discerning rolling over for the care recipient computed by the bed sensor output processing section 113 based on a plurality of detected signals repeatedly detected by the bed sensor 35 during the time period;

a plurality of body movement indicators for discerning between body movement and resting for the care recipient computed by the bed sensor output processing section 113 based on a plurality of detected signals repeatedly detected by the bed sensor 35 during the time period; and a plurality of sleep indicators for discerning between sleeping and waking for the care recipient computed by the bed sensor output processing section 113 based on a plurality of detected signals repeatedly detected by the bed sensor 35 during the time period. A higher value of the bed-leaving prediction value implies higher possibility of bed-leaving after the second time interval expires, and a lower value implies lower possibility of bed-leaving after the second time interval expires.

It is preferable to determine feature values or fundamental statistics during the time period (for 30 minutes) for each of the temperature, the humidity, the illuminance, the movement-amount indicator, the pulse rate indicator, the posture indicator, the rolling-over indicator, the body movement indicator, and the sleep indicator, and calculate the bed-leaving prediction value based on the feature values or fundamental statistics. Practically, for processing of calculation of the bed-leaving prediction value from the feature values or fundamental statistics, Artificial Intelligence (AI) technology is employed.

In other words, the bed-leaving prediction processing may preferably be implemented by a neural network. More preferably, the bed-leaving prediction processing is implemented by a multi-layer neural network (deep learning). A program for training such a neural network is stored in the storage section 103, and the learning program (learning section) trains the neural network using the bed-leaving indicator as training data along with information that identifies a care recipient, environment values such as temperature, humidity, and illuminance detected by the environmental sensor installed in a room where the care recipient stays, the movement-amount indicator, the pulse rate, the posture indicator, the rolling-over indicator, the body movement indicator, and the sleep indicator.

Examples of feature value and fundamental statistics include an average, a standard deviation, a minimum value, a maximum value, and three types of quartiles (25%, 50%, 75%) in the time period. Practically, at least one of fundamental statistics specified for each indicator is applied for a process of estimating the bed-leaving prediction value. Feature values or fundamental statistics practically applied for the process of estimating the bed-leaving prediction value are preferably be applied by being combined as necessary for each care recipient depending on the nature of sleeping, waking, or bed-leaving of the care recipient and even for each of the temperature, the humidity, the illuminance, the movement-amount indicator, the pulse rate, the posture indicator, the rolling-over indicator, the body movement indicator, and the sleep indicator.

The bed-leaving prediction processing section 115 compares the estimated bed-leaving prediction value with a threshold value stored in the storage section 103 in advance. When the bed-leaving prediction value exceeds the threshold value, the bed-leaving notification processing section 117 transmits, through the terminal communication section 107 to the portable information processing terminal 40, a bed-leaving notification indicating that the care recipient leaves the sleeping furniture 70 after the second time interval, typically 30 minutes, which is the same as the first time interval, has expired since the current time point (prediction calculation processing time point). When the bed-leaving prediction value is equal to or less than the threshold value, the bed-leaving notification is not transmitted to the portable information processing terminal 40.

On the display screen of the portable information processing terminal 40 that has received the bed-leaving notification, a message to the effect that the care recipient will leave the sleeping furniture 70 after 30 minutes expire is displayed, and at the same time, three types of buttons corresponding to commands for transmitting (as a reply) a bed-leaving prediction result to the bed-leaving prediction notification device 10 are displayed so that a situation in which the care staff who arrived at the room could care for the care recipient leaving the bed (first situation), a situation in which the care staff arrived at the room and waited for a while but the care recipient did not leave the bed (second situation), or a situation in which the care recipient had already left the bed before the care staff arrived at the room (third situation) are distinguished. When the care staff clicks on any of the three types of buttons, information indicative of any of the first to third situations is transmitted from the portable information processing terminal 40 to the bed-leaving prediction notification device 10.

When the first situation ("bed-leaving care successful") is received from the portable information processing terminal 40 as the bed-leaving prediction result, the control section 101 of the bed-leaving prediction notification device 10 maintains the threshold value stored in the storage section 103 as it is at the current value. On the other hand, when the second situation ("did not leave the bed") is received from the portable information processing terminal 40 as the bed-leaving prediction result, the control section 101 controls the storage section 103 to update the threshold value stored in the storage section 103 to a higher value by adding a predetermined value, for example 5%, to the current value. When the third situation ("already left the bed") is received from the portable information processing terminal 40 as the bed-leaving prediction result, the control section 101 controls the bed-leaving prediction processing section 115 to update the threshold value to be applied to the bed-leaving prediction processing from the current value to a lower value by subtracting a predetermined value, for example 5%.

The initial value of the above-described threshold value, the added value added to the threshold value in the second situation, the subtracted value subtracted from the threshold value in the third situation, and the first and second time intervals used in the bed-leaving estimating processing may be set by the facility manager for each care recipient individually through the information processing device 20 for comprehensive management.

Figure 5:
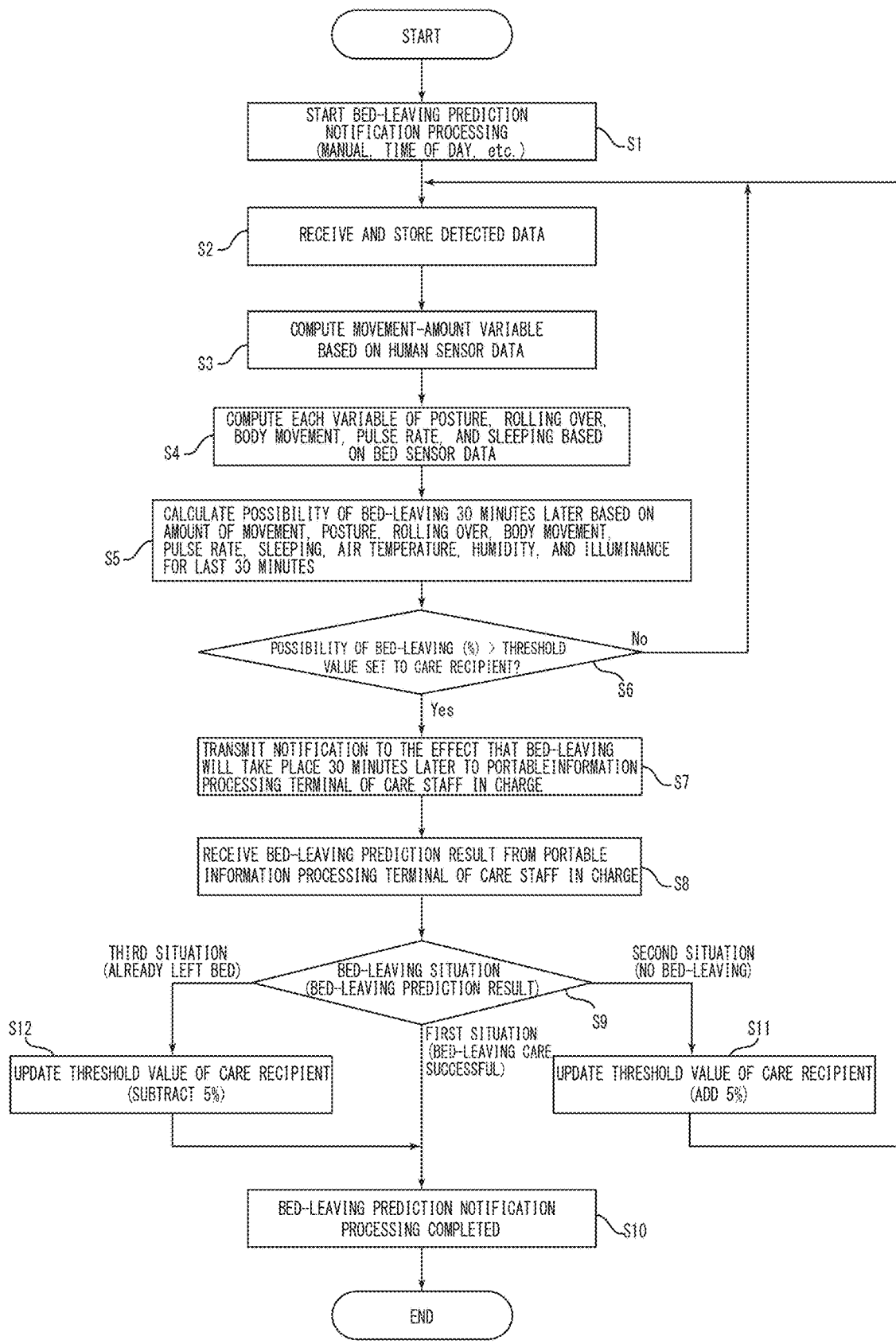
FIG. 5 is a flow chart illustrating a bed-leaving prediction notification processing procedure performed by the bed-leaving prediction notification device in FIG. 1.
Figure 6:
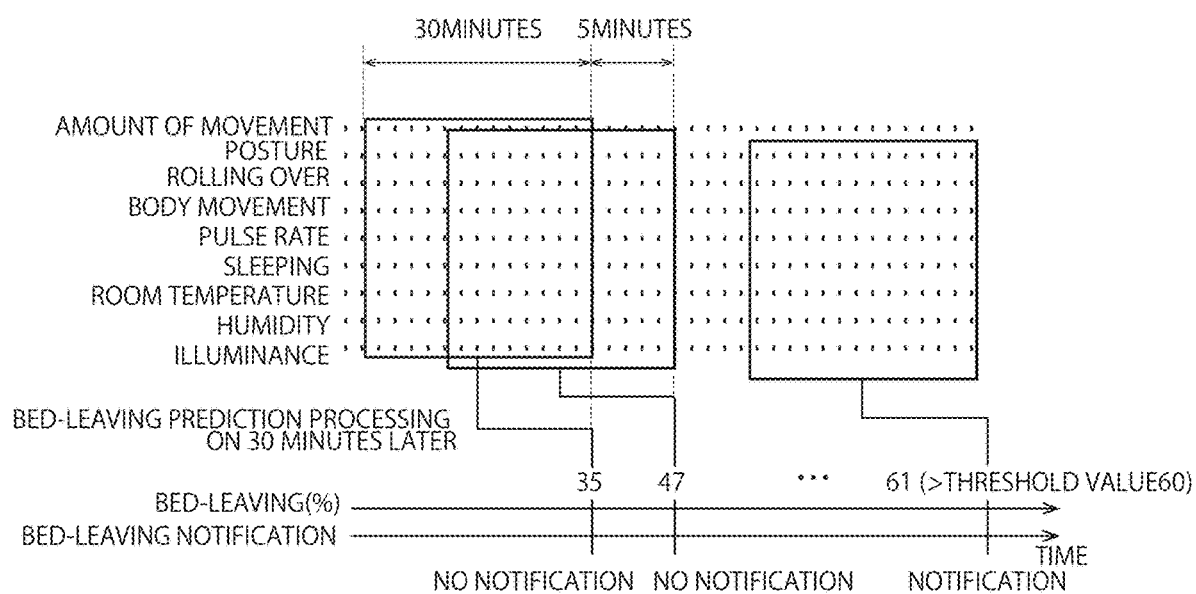
FIG. 6 is a supplementary view of the processing procedure in FIG. 5.

FIG. 5 illustrates a bed-leaving prediction notification processing procedure according to the embodiment. FIG. 6 is a supplementary view of the processing procedure in FIG. 5. First, at step S1, the bed-leaving prediction notification processing is started. The processing can be started either for each room individually or for a plurality of rooms in the facility collectively. Further, the processing can be started either manually or automatically according to set time of day. Triggered by the start of the bed-leaving prediction notification processing, detected data of the human sensor 31, the temperature sensor 32, the humidity sensor 33, the illuminance sensor 34, and the bed sensor 35 are received by the bed-leaving prediction notification device 10 through the gateway device 50 and stored in the storage section 103 by being associated with the room identification number and detected time of day (S2).

The movement-amount indicator, which reflects the amount of movement of the care recipient on the sleeping furniture 70, is computed by the human sensor output processing section 111 based on the detected data of the human sensor 31 and stored in the storage section 103 (S3). Further, the pulse rate, the posture indicator, the rolling-over indicator, the body movement indicator, and the sleep indicator of the care recipient are computed by the bed sensor output processing section 113 based on detected data of the microphones 359 to 362 of the bed sensor 35 and stored in the storage section 103 (S4).

Next, the bed-leaving prediction value (%) indicating that the care recipient leaves the sleeping furniture 70 at a time point after 30 minutes has expired since the current time point (prediction calculation processing time point) is calculated by the bed-leaving prediction processing section 115 based on a plurality of values of temperature, a plurality of values of humidity, a plurality of values of illuminance, a plurality of movement-amount indicators, a plurality of pulse rates, a plurality of posture indicators, a plurality of rolling-over indicators, a plurality of body movement indicators, and a plurality of sleep indicators, which have been generated in the time period between the current time point and the time point before expiration of 30 minutes (S5). In the bed-leaving prediction processing section 115, the bed-leaving prediction value is compared with the threshold value set for the care recipient in advance (S6). The bed-leaving prediction value is repeatedly calculated in a predetermined cycle, for example 5-minute cycle, and compared with the threshold value.

When the bed-leaving prediction value is equal to or less than the threshold value, that is, when it is determined that the possibility that the care recipient leaves the sleeping furniture 70 at the time point after 30 minutes expire is low (S6: No), the process returns to step S2. When the bed-leaving prediction value exceeds the threshold value, that is, it is determined that the possibility that the care recipient leaves the sleeping furniture 70 at the time point after 30 minutes expire is high (S6: Yes), notification to the effect that "will leave the bed 30 minutes later" is transmitted to the portable information processing terminal 40 of the care staff taking care of the care recipient with information of the room number and the name of the care recipient from the bed-leaving notification processing section 117 through the terminal communication section 107 (S7). When the bed-leaving prediction value is equal to or less than the threshold value, it is preferable that any notification to the effect that "the care recipient will leave the bed 30 minutes later", and even notification to the effect that "the care recipient is less likely to leave the bed 30 minutes later" will not be transmitted to the portable information processing terminal 40.

Figure 7:
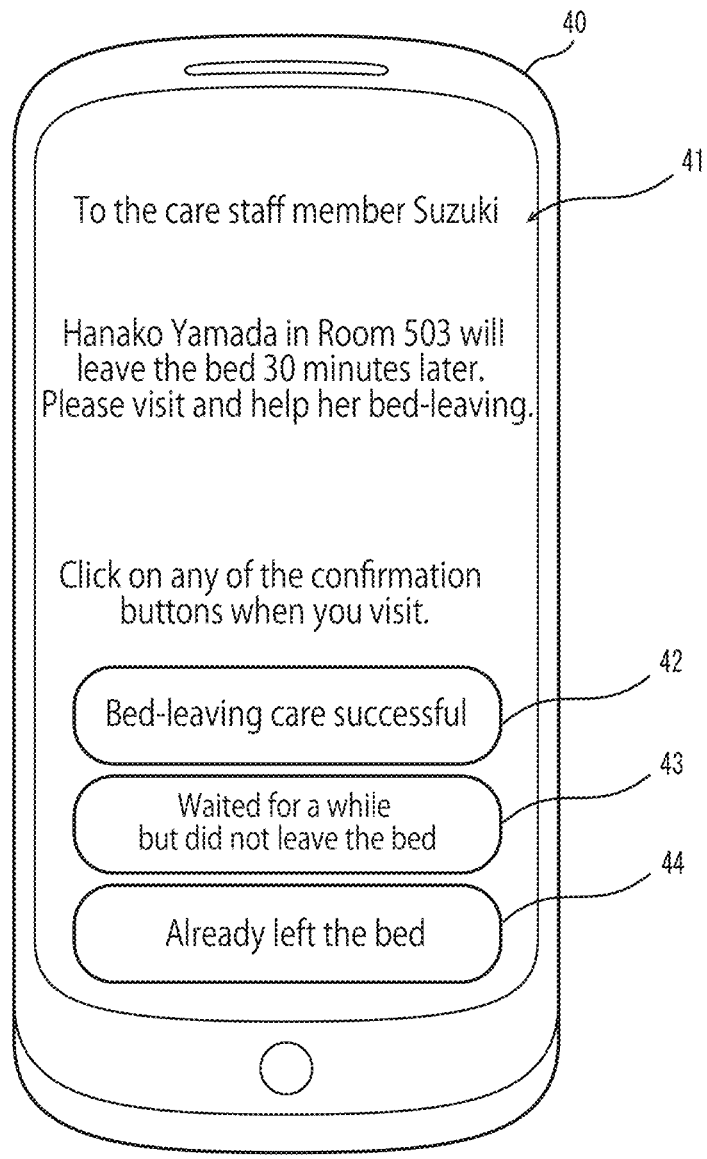
FIG. 7 illustrates an example display screen of an information processing terminal carried by care staff that is corresponding to step S8 in FIG. 5.

As illustrated in FIG. 7, on the display screen of the portable information processing terminal 40, a message 41, such as "the care recipient will leave the bed 30 minutes later" is displayed with the room number and the name identifying the care recipient. On the screen, three types of buttons 42, 43, and 44 are displayed for notifying any of a situation in which the care staff who arrived at the room could care for the care recipient leaving the bed (first situation), a situation in which the care staff arrived at the room and waited for a while but the care recipient did not leave the bed (second situation), and a situation in which the care recipient had already left the bed before the care staff arrived at the room (third situation) to the bed-leaving prediction notification device 10 as the bed-leaving prediction result. When the care staff clicks on any of the three types of buttons 42, 43, and 44, information indicative of any of the first to third situations is transmitted as the bed-leaving prediction result from the portable information processing terminal 40 to the bed-leaving prediction notification device 10 (S8). The bed-leaving prediction result is input through an input layer of Artificial Intelligence (AI) with temperature, humidity, illuminance, a movement-amount indicator, a pulse rate indicator, a posture indicator, a rolling-over indicator, a body movement indicator, and a sleep indicator (or feature values or fundamental statistics) and used to improve estimation accuracy.

According to the reception from the portable information processing terminal 40, the bed-leaving prediction result is discriminated by the control section 101 of the bed-leaving prediction notification device 10 (S9). When the bed-leaving prediction result is the first situation ("bed-leaving care successful"), the bed-leaving prediction processing and the bed-leaving notification processing come to an end because it is decided that the bed-leaving prediction was accurate (S10). When the bed-leaving prediction result is the second situation ("did not leave the bed"), because it is decided that the bed-leaving prediction was inaccurate and the bed-leaving prediction was too early, the current threshold value associated with the care recipient is updated to a higher value by adding a predetermined value, for example 5%, to the threshold value (S11), and the process returns to step S2 to continue the bed-leaving prediction processing and the notification processing. With the increased threshold value, the bed-leaving prediction accuracy for the next time can be improved. When the bed-leaving prediction result is the third situation ("already left the bed"), because it is decided that the bed-leaving prediction was inaccurate and the bed-leaving prediction was too late, the current threshold value associated with the care recipient is updated to a lower value by subtracting a predetermined value, for example 5%, from the threshold value (S12), and the bed-leaving prediction processing and the bed-leaving notification processing come to an end (S10). With the lower threshold value, the bed-leaving prediction accuracy for the next time can be improved. Repeating the bed-leaving prediction processing, the notification processing, and updating processing of the threshold value according to the bed-leaving prediction result over several days and several weeks can contribute to further improvement in accuracy of the bed-leaving prediction.

As described above, based on various types of information such as environmental information of the room (temperature, humidity, illuminance), physiologic information of the care recipient (pulse rate), action information of the care recipient on the sleeping furniture (movement-amount indicator, posture indicator, rolling-over indicator, body movement indicator), and sleep information of the care recipient (sleep indicator) over a relatively long time period of at least 10 minutes, typically 30 minutes, it is possible to accurately predict bed-leaving of the care recipient at a time point after a relatively long time such as after at least 10 minutes expire, typically 30 minutes expire, and allow the care staff to visit and care for before the care recipient leaves the bed.

Figure 8:
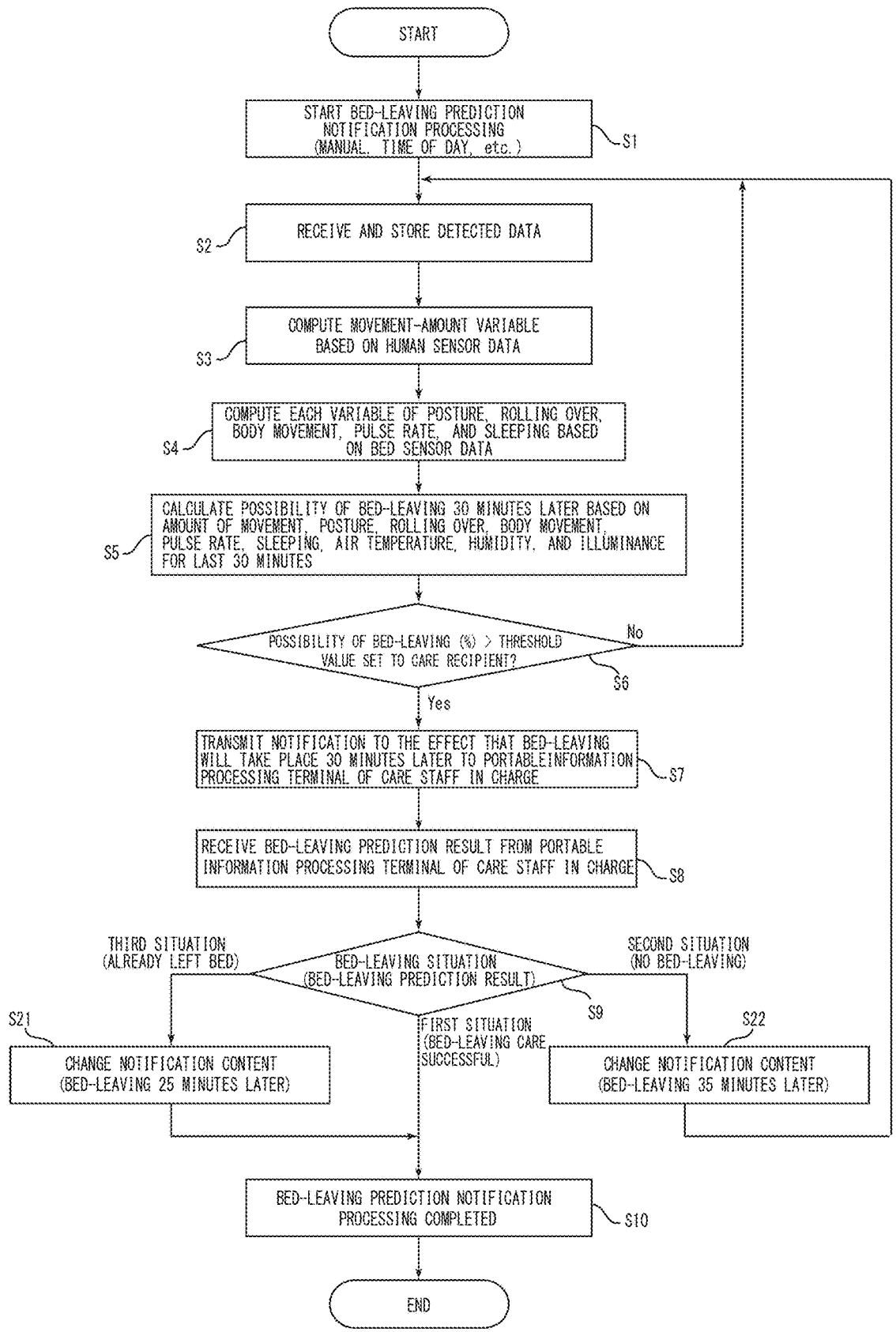
FIG. 8 is a flow chart illustrating a variation of the bed-leaving prediction notification processing in FIG. 5.

In the above description, when the bed-leaving prediction result is the second situation ("did not leave the bed") or the third situation ("already left the bed"), the threshold value is updated. However, instead of being updated, the threshold value may be maintained, and message contents of the bed-leaving notification may be changed. As illustrated in FIG. 8, when the bed-leaving prediction result is the second situation ("did not leave the bed"), the message content "will leave the bed 30 minutes later" of the bed-leaving notification at the current time point is updated to the message content "will leave the bed 35 minutes later" for a new bed-leaving notification by adding a predetermined time, typically 5 minutes, to the expiration time (30 minutes at the current time point) written in the message content. When the bed-leaving prediction result is the third situation ("already left the bed"), the message content "will leave the bed 30 minutes later" of the bed-leaving notification at the current time point is updated to the message content "will leave the bed 25 minutes later" for a new bed-leaving notification by subtracting a predetermined time, typically 5 minutes, from the expiration time (30 minutes at the current time point) written in the message content. Repeating the bed-leaving prediction processing, the notification processing, and updating processing of the threshold value according to the bed-leaving prediction result over several days and several weeks can allow a notified bed-leaving timing to match with an actual bed-leaving timing.

Some embodiments of the present invention have been described. However, the embodiments are presented only for an illustrative purpose, and are not intended to limit the scope of the invention. The embodiments can be implemented in various other forms, and may be subjected to various omission, substitution, and alteration without departing from the spirit of the invention. The embodiments and variations thereof are included within the scope and spirit of the invention as well as within the scope of the invention according to claims and equivalents thereof.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

REFERENCE SIGNS LIST

10 . . . bed-leaving prediction notification device, 20 . . . information processing device for comprehensive management, 30 . . . sensor group, 31 . . . human sensor, 32 . . . temperature sensor, 33 . . . humidity sensor, 34 . . . illuminance sensor, 35 . . . bed sensor, 40 . . . portable information processing terminal, 101 . . . control section, 102 . . . control/data bus, 103 . . . storage section, 105 . . . timer circuit, 107 . . . terminal communication section, 109 . . . gateway communication section, 111 . . . human sensor output processing section, 113 . . . bed sensor output processing section, 115 . . . bed-leaving prediction processing section, 117 . . . bed-leaving notification processing section

The invention claimed is:

1. A bed-leaving prediction server device connected through a digital communication network to: an information processing terminal for care staff who care for a care recipient; an environmental sensor configured to detect at least one environment value of temperature, humidity, and illuminance in a room where the care recipient stays; an infrared sensor installed to include a sleeping furniture in the room in a sensing area; and a sleeping furniture sensor configured to detect movement of the care recipient on the sleeping furniture, the bed-leaving prediction server device comprising:

a computing section configured to repeatedly compute, based on an output of the infrared sensor, a movement-amount indicator that depends on an amount of movement of the care recipient on the sleeping furniture, and configured to repeatedly compute, based on an output of the sleeping furniture sensor, a pulse rate of the care recipient, a posture indicator for discerning a posture: lying flat; sitting; or sitting up with legs outstretched, a rolling-over indicator for discerning rolling over: rolling over to left; leftward movement; rightward movement; rolling over to right; or no movement, a body movement indicator for discerning between body movement and resting states, and a sleep indicator for discerning between sleeping and waking;

a calculating section configured to calculate a bed-leaving prediction value indicative of a degree of possibility that the care recipient leaves the sleeping furniture after a second time interval has expired since a prediction calculation processing time point based on: a plurality of the environment values detected in a time period between the prediction calculation processing time point and a time point before expiration of a first time interval; and a plurality of the movement-amount indicators, a plurality of the pulse rates, a plurality of the posture indicators, a plurality of the rolling-over indicators, a plurality of the body movement indicators, and a plurality of the sleep indicators, which are computed based on outputs of the sleeping furniture sensor in the time period; and a notification processing section configured to transmit a bed-leaving notification to the information processing terminal when the bed-leaving prediction value exceeds a threshold value, the bed-leaving notification indicating that the care recipient leaves the sleeping furniture after the second time interval expires.

2. The bed-leaving prediction server device according to claim 1, further comprising a receiving section configured to receive, from the information processing terminal as a bed-leaving prediction result, any of information indicative of a first situation in which the care staff who received the bed-leaving notification could care for the care recipient leaving the sleeping furniture, and information indicative of a second situation in which the care recipient did not leave the sleeping furniture, wherein when information indicative of the first situation is received from the information processing terminal as the bed-leaving prediction result, the threshold value is maintained, and when information indicative of the second situation is received, the threshold value is updated to a new threshold value by adding a predetermined value to the previous threshold value.

3. The bed-leaving prediction server device according to claim 1, further comprising a receiving section configured to receive, from the information processing terminal as a bed-leaving prediction result, any of information indicative of a first situation in which the care staff who received the bed-leaving notification could care for the care recipient leaving the sleeping furniture, and information indicative of a second situation in which the care recipient did not leave the sleeping furniture, wherein when information indicative of the first situation is received from the information processing terminal as the bed-leaving prediction result, the bed-leaving notification indicating that the care recipient leaves the sleeping furniture after the second time interval expires is maintained, and when information indicative of the second situation is received, the bed-leaving notification is updated to a bed-leaving notification indicating that the care recipient leaves the sleeping furniture after a third time interval that is longer than the second time interval expires.

4. The bed-leaving prediction server device according to claim 1, further comprising a receiving section configured to receive, from the information processing terminal as the bed-leaving prediction result, any of information indicative of a first situation in which the care staff who received the bed-leaving notification could care for the care recipient leaving the sleeping furniture, information indicative of a second situation in which the care recipient did not leave the sleeping furniture, and information indicative of a third situation in which the care recipient had already left the sleeping furniture before the care staff arrived at the room,
 wherein when information indicative of the first situation is received from the information processing terminal as the bed-leaving prediction result, the threshold value is maintained, and when information indicative of the second situation is received, the threshold value is replaced with a new threshold value by adding a predetermined value to the previous threshold value, and when information indicative of the third situation is received, the threshold value is replaced with a new threshold value by subtracting a predetermined value from the previous threshold value.

5. The bed-leaving prediction server device according to claim 1, further comprising a receiving section configured to receive, from the information processing terminal as the bed-leaving prediction result, any of information indicative of a first situation in which the care staff who received the bed-leaving notification could care for the care recipient leaving the sleeping furniture, information indicative of a second situation in which the care recipient did not leave the sleeping furniture, and information indicative of a third situation in which the care recipient had already left the sleeping furniture before the care staff arrived at the room,
 wherein when information indicative of the first situation is received from the information processing terminal as the bed-leaving prediction result, the bed-leaving notification indicating that the care recipient leaves the sleeping furniture after the second time interval expires is maintained, and when information indicative of the second situation is received, the bed-leaving notification is updated to a bed-leaving notification indicating that the care recipient leaves the sleeping furniture after a third time interval that is longer than the second time interval expires, and when information indicative of the third situation is received, the bed-leaving notification is updated to a bed-leaving notification indicating that the care recipient leaves the sleeping furniture after a fourth time interval that is shorter than the second time interval expires.

6. The bed-leaving prediction server device according to claim 1, wherein the threshold value is associated with the care recipient individually.

7. A non-transitory storage medium storing a program causing a computer to implement:
 connecting through a digital communication network to: an information processing terminal for care staff who care for a care recipient; an environmental sensor configured to detect at least one environment value of temperature, humidity, and illuminance in a room where the care recipient stays; an infrared sensor installed to include a sleeping furniture in the room in a sensing area; and a sleeping furniture sensor configured to detect movement of the care recipient on the sleeping furniture;
 repeatedly computing, based on an output of the infrared sensor, a movement-amount indicator that depends on an amount of movement of the care recipient on the sleeping furniture, and repeatedly computing, based on an output of the sleeping furniture sensor, a pulse rate (heart rate) of the care recipient, a posture indicator for discerning a posture: lying flat; sitting; or sitting up with legs outstretched, a rolling-over indicator for discerning rolling over: rolling over to left; leftward movement; rightward movement; rolling over to right; or no movement, a body movement indicator for discerning between body movement and resting states, and a sleep indicator for discerning between sleeping and waking;
 calculating a bed-leaving prediction value indicative of a degree of possibility that the care recipient leaves the sleeping furniture after a second time interval has expired since a prediction calculation processing time point based on: a plurality of the environment values detected in a time period between the prediction calculation processing time point and a time point before expiration of a first time interval; and a plurality of the movement-amount indicators, a plurality of the pulse rates (heart rates), a plurality of the posture indicators, a plurality of the rolling-over indicators, a plurality of the body movement indicators, and a plurality of the sleep indicators, which are computed based on outputs of the sleeping furniture sensor in the time period; and
 comparing the bed-leaving prediction value with a threshold value, and transmitting a bed-leaving notification to the information processing terminal when the bed-leaving prediction value exceeds the threshold value, the bed-leaving notification indicating that the care recipient leaves the sleeping furniture after the second time interval expires.

8. A bed-leaving prediction device implementing a neural network, the bed-leaving prediction device comprising:
 a computing section configured to compute a movement-amount indicator that depends on an amount of movement of a care recipient on a sleeping furniture based on an output of an infrared sensor installed to include the sleeping furniture in a room in a sensing area;
 a computing section configured to compute, based on an output of a sleeping furniture sensor installed on the sleeping furniture, a pulse rate of the care recipient, a posture indicator for discerning a posture: lying flat; sitting; or sitting up with legs outstretched, a rolling-over indicator for discerning rolling over: rolling over to left; leftward movement; rightward movement; rolling over to right; or no movement, a body movement indicator for discerning between body movement and resting states, a sleep indicator for discerning between sleeping and waking, and a bed-leaving indicator for discerning between recumbency and bed-leaving;
 a learning section configured to train the neural network by using the bed-leaving indicator as training data along with information that identifies the care recipient, at least one environment value of temperature, humidity, and illuminance detected by an environmental sensor installed in a room where the care recipient stays, the movement-amount indicator, the pulse rate, the posture indicator, the rolling-over indicator, the body movement indicator, and the sleep indicator; and
 a bed-leaving prediction section configured to input the environment value, a pulse rate of the care recipient, the posture indicator, the rolling-over indicator, the body movement indicator, and the sleep indicator at current time of day to the trained neural network, and configured to output a bed-leaving prediction value indicative of a degree of possibility that the care recipient leaves the sleeping furniture after a predetermined time has expired since the current time of day.

* * * * *